United States Patent [19]
Bass, Jr. et al.

[11] Patent Number: 5,533,523
[45] Date of Patent: Jul. 9, 1996

[54] MEDICAL MOUTHPIECE

[76] Inventors: Robert Bass, Jr., 35 Rosewood Dr., Jacksonville Beach, Fla. 32250; James G. Barsamian, 1996 Raley Creek Dr. West, Jacksonville, Fla. 32225

[21] Appl. No.: 442,197

[22] Filed: May 16, 1995

[51] Int. Cl.⁶ .................................................. A61C 5/14
[52] U.S. Cl. ........................................... 128/859; 128/861
[58] Field of Search .................... 128/859–862, 128/62 A, 848; 2/2

[56] References Cited

U.S. PATENT DOCUMENTS

| | | | |
|---|---|---|---|
| 2,669,988 | 2/1954 | Carpenter | 128/861 |
| 3,139,088 | 6/1964 | Galleher | 128/859 |
| 4,425,911 | 1/1984 | Luomanen | 128/862 |
| 4,928,710 | 5/1990 | Campbell | 128/861 |
| 5,174,284 | 12/1992 | Jackson | 128/859 |

*Primary Examiner*—Michael A. Brown
*Attorney, Agent, or Firm*—Arthur G. Yeager; Earl L. Tyner

[57] ABSTRACT

A hollow tubular mouthpiece that is clampable between the front teeth of a patient that is to receive a medical instrument through the mouth and into the esophagus. The mouthpiece has two spaced flanges to fit over the outside of the lips on the proximal end of the mouthpiece and behind the front teeth on the distal end of the mouthpiece with the intermediate space to be clamped between the biting front teeth. A central hollow passageway permits the instrument to be inserted. A lower curved tongue plate extends inwardly and downwardly to depress the patients tongue and to guide the forward end of the instrument.

10 Claims, 4 Drawing Sheets

MEDICAL MOUTHPIECE

FIELD OF THE INVENTION

This invention relates to medical instruments; particularly to mouthpieces to facilitate the introduction of instruments into the esophagus, stomach and surrounding cavities.

BACKGROUND OF THE INVENTION

There are many instances when the practice of medicine requires an examination of or a treatment of the esophagus, stomach upper intestine, etc., by means that pass through the mouth and into the throat. Any foreign solid object introduced into the mouth normally causes the patient to gag, which may be life threatening. Physicians, surgeons, dentists, etc. have developed techniques and procedures to counteract or minimize the tendency to gag. Among such procedures are the use of special anesthetics, and devices to hold the mouth open. Typical of such devices is that of U.S. Pat. No. 4,944,313 wherein a three-piece construction including a forward flange and a rearward flange joined together by a central soft elastic tubular unit which is clamped between the upper and lower teeth of the patient. This device is useful for the intended purpose, but it fails in certain aspects which the present invention provides.

Accordingly, it is an object of the present invention to provide a novel medical mouthpiece. It is another object of this invention to provide a novel mouthpiece to facilitate the introduction of a medical instrument into the patient's esophagus, while substantially eliminating gagging by the patient. Still other objects of the invention will appear from a study of the more detailed description which follows.

BRIEF DESCRIPTION OF THE INVENTION

The invention relates to a mouthpiece to facilitate the introduction of a medical instrument into the esophagus of a patient, the mouthpiece comprising a hollow tubular structure with an outer convex flange to fit over the lips of the patient and an inner flange to fit inside the incisor teeth of the patient, an annular hollow tubular connecting bridge member adapted to receive the biting action of said incisor teeth, said hollow being centrally located and extending from the outside of said outer flange to the inside of said inner flange, and an inwardly extending downwardly curving plate attached to the lower portion of said inner flange and adapted to lie above and to depress the patient's tongue.

In specific and preferred embodiments of the invention the longitudinal axis of the mouthpiece is tilted upwards from the horizontal an amount of about 15 degrees to 18 degrees to facilitate the entry of a medical instrument into the esophagus, and the hollow passageway of the mouthpiece is elliptical in lateral cross-section.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The mouthpiece of this invention is best understood in the following description taken in conjunction with the attached drawings.

Figure 1:
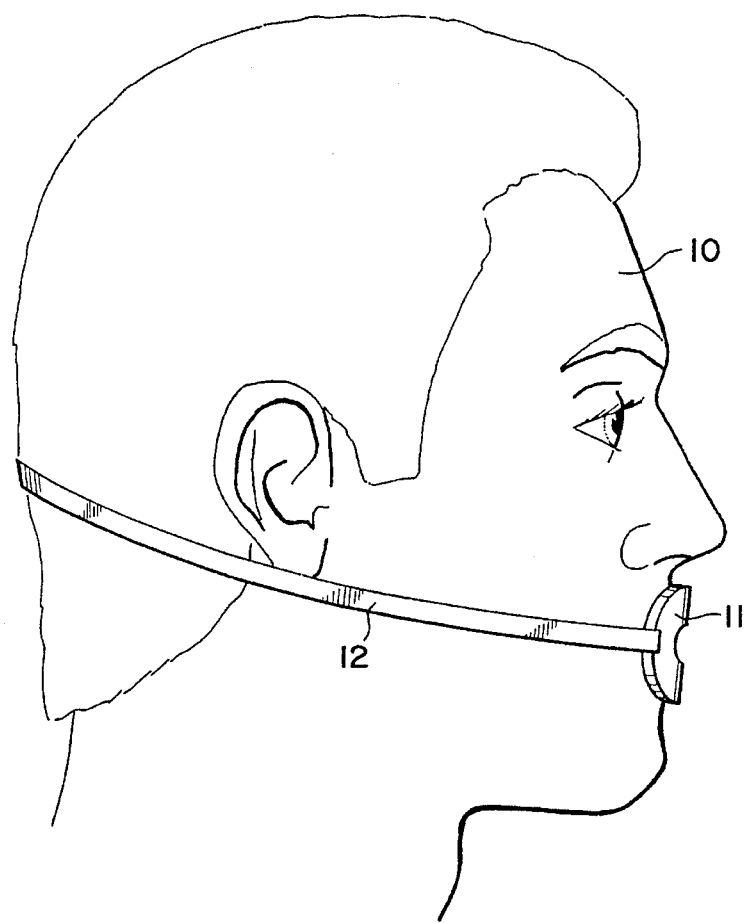
FIG. 1 is a side elevational view of a patient wearing the mouthpiece of this invention.
Figure 2:
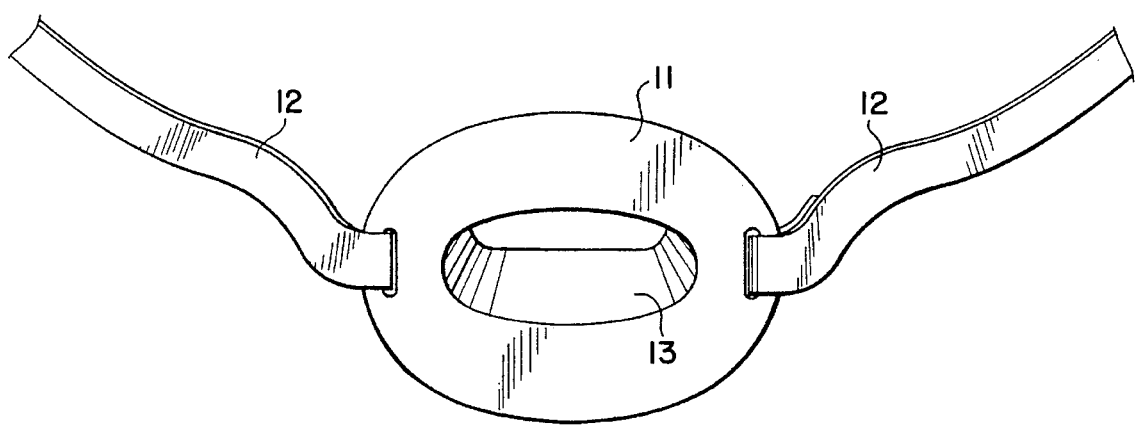
FIG. 2 is a perspective view of the mouthpiece of this invention.

FIGS. 1 and 2 show a patient 10 with a mouthpiece 11 in the patient's mouth and an elastic headband 12 holding the mouthpiece 11 with a hollow passageway 13 in the patient's mouth.

Figure 3:
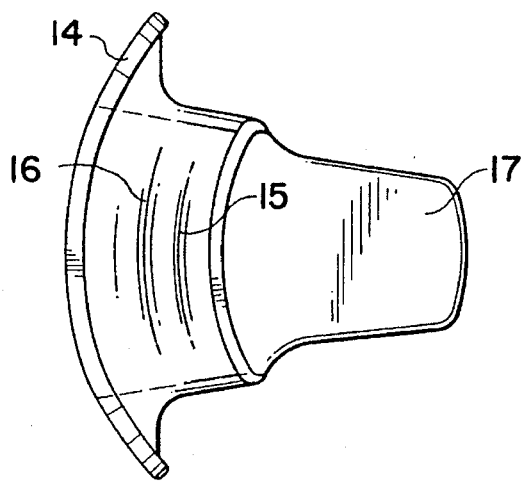
FIG. 3 is a top plan view of the mouthpiece of this invention.
Figure 4:
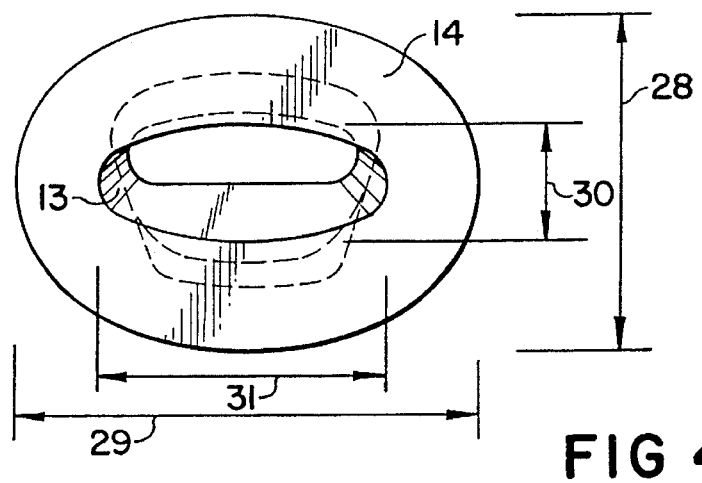
FIG. 4 is a front elevational view of the mouthpiece of this invention.
Figure 5:
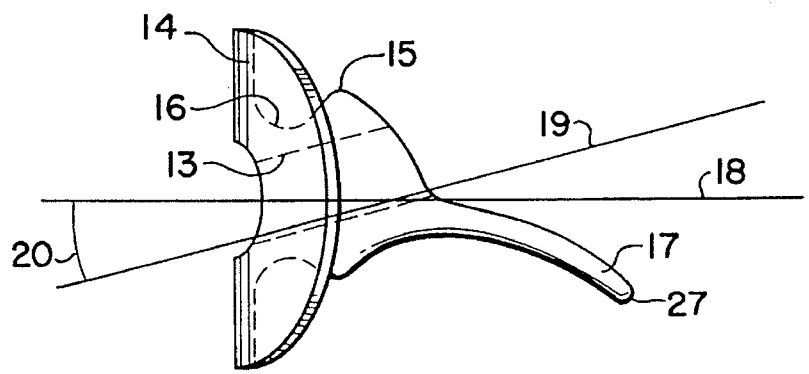
FIG. 5 is a side elevational view of the mouthpiece of this invention.

In FIGS. 3, 4, and 5 the details of the structure of mouthpiece 11 can be seen. There is an outer or proximal flange 14 that covers the facial surface of the lips and an inner flange 15 which fits inside the front teeth (incisors) 22, 23 of the patient so that a biting action of the teeth 22, 23 clamps the mouthpiece firmly in place. A recess between flanges 14 and 15 allows the lips of the patient to be protected and comfortably held in place. The outer flange 14 is slightly curved so as to fit the generally convex contours of the face and lips of the patient. The space between outer flange 14 and inner flange 15 is occupied by a hollow tubular connecting member 16 through which runs a longitudinal hollow 13 which is generally elliptical in lateral cross section. It may be seen in FIG. 5 that hollow 13 is tilted upwardly from the horizontal such that as an instrument is passed into and through hollow 13 from outer flange 14 to inner flange 15 the instrument rises in elevation. The amount of tilt is shown in FIG. 5 as an angle 20 between the horizontal 18 and the axis 19 of hollow 13. This angle is preferably about 15 degrees to 18 degrees. The advantage of such an upward tilt will be discussed below. A final feature of the mouthpiece is tongue depressor plate 17 which extends rearwardly and curves downwardly from the lower portion of hollow 13. The horizontal extension of plate 17 from the outer surface of flange 14 to the inner end 27 is about 40–60 mm. The vertical height of mouthpiece 11 is about 40–50 mm, preferably about 45 mm. The horizontal width of mouthpiece 11 is about 60–70 mm, preferably about 63 mm. The vertical height of the hollow 13 is about 10–20 mm, preferably about 14 mm. The horizontal width of hollow 13 is about 35–45 mm, preferably about 38 mm. The mouthpiece may be made of stainless steel, aluminum, or other metals, but preferably is molded plastic, e.g., polyolefin, polyacetal, polycarbonate, or the like.

Figure 6:
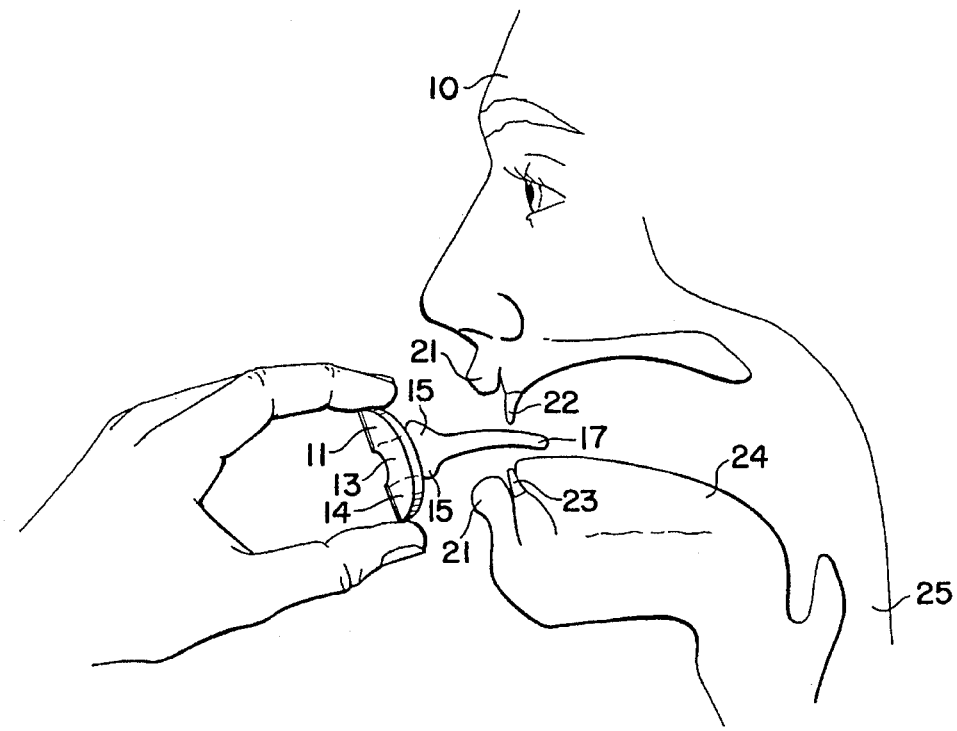
FIG. 6 is a side elevational view, partly in cross-section, of a patient with the mouthpiece of this invention being inserted into his mouth.
Figure 8:
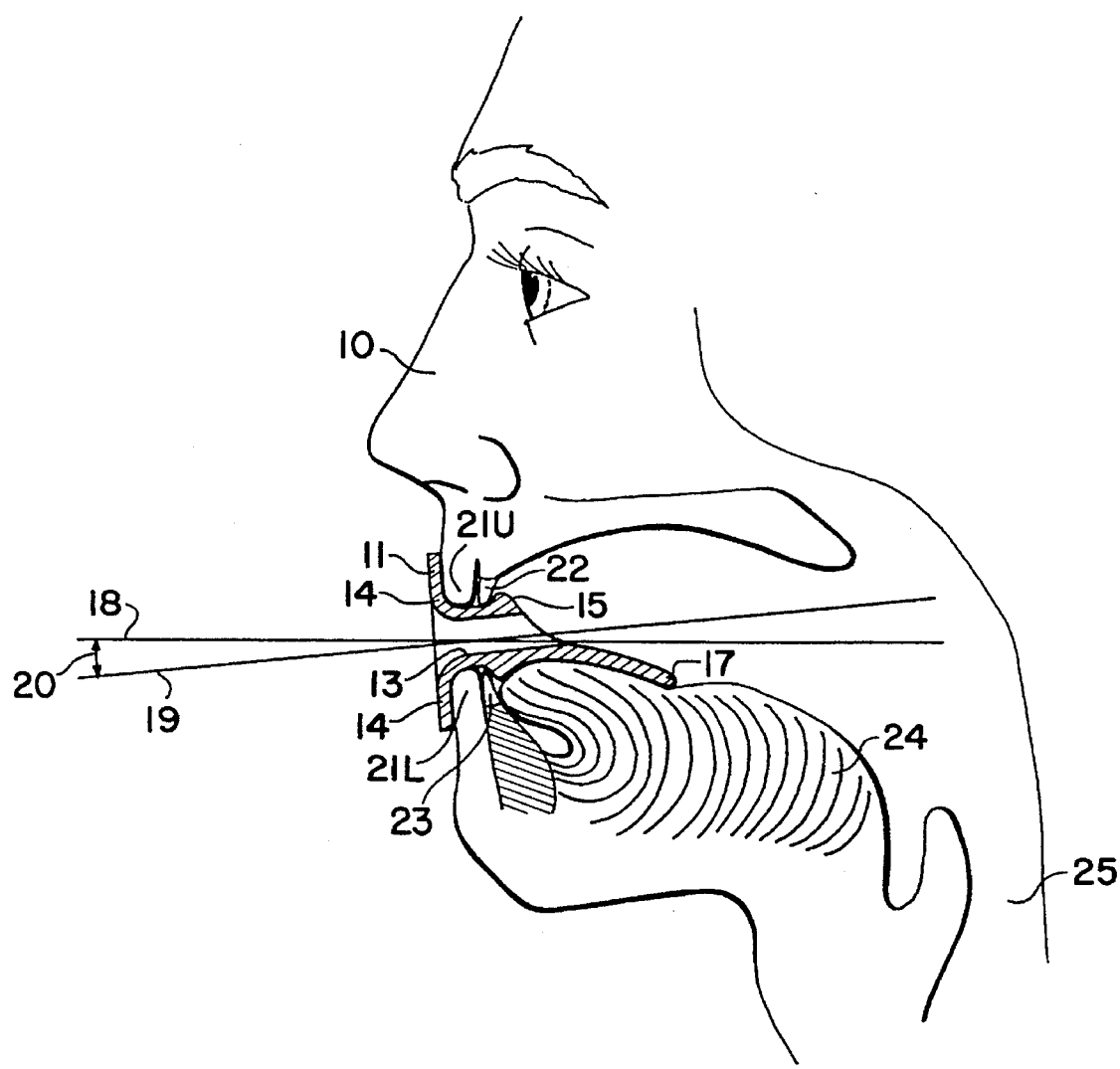
FIG. 8 is a side cross-sectional view of the mouthpiece of this invention in place in the patient's mouth.

FIGS. 6 and 8 show how the mouthpiece is used. In FIG. 6 the mouthpiece 11 is being inserted into the mouth of patient 10 with tongue depressing plate 17 leading the way into the mouth to lie on top of tongue 24 and the teeth, incisors 22 and 23 to bite down forward of inner flange 15 and lips 21 to be behind outer flange 14. In FIG. 8 the mouth is closed upon mouthpiece 11 with lips 21U and 21L being behind outer flange 14 and teeth 22 and 23 biting toward each other forward of inner flange 15. Tongue 24 is kept in place with tongue depressor plate 17.

Figure 7:
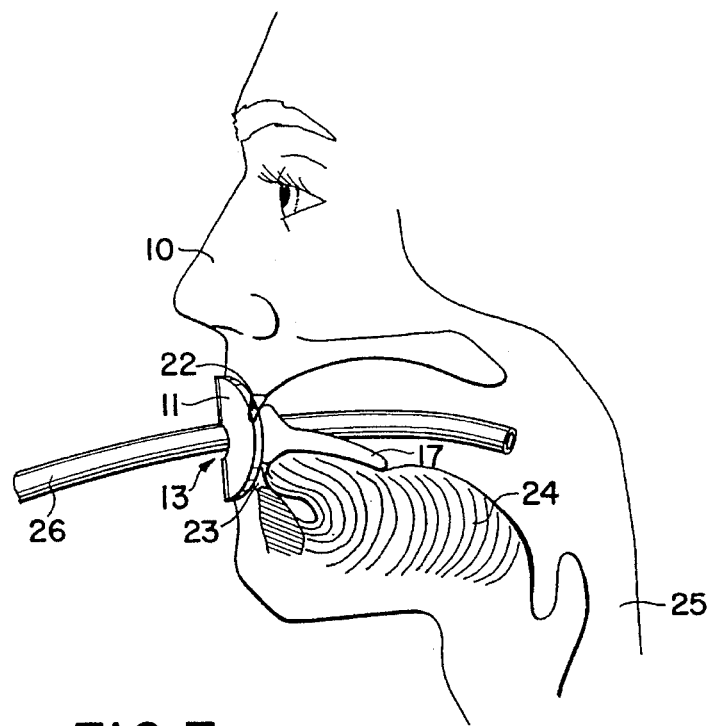
FIG. 7 is a side elevational view similar to that of FIG. 6 of the mouthpiece which has been inserted into place and a medical instrument is inserted through the mouthpiece.

FIG. 7 shows how a tube or an instrument 26 is then inserted through hollow 13 to reach the upper end of esophagus 25 or any available area deeper in the oral cavity.

The general medical procedure for endoscopic examination and surgical procedure starts when the patient is brought into the specialized endoscopy suite of the hospital or outpatient surgery center. After consent is obtained and signed, and the patient understands the risks of the procedure to be bleeding, perforation, and possible allergy to intravenous sedative medications, the patient is placed in the left prone position. The oral pharynx and posterior pharynx is sprayed with a suitable anesthetic in order to diminish the gag response and diminish sensation in the posterior pharynx. After the posterior pharynx has been properly anesthetized, a plastic mouth protector is placed between the patient's teeth and is secured with a strap. The purpose of the mouthpiece is to enable the endoscope to be easily passed over the teeth and tongue. In addition, the mouthpiece serves to protect the endoscope from accidental damage, i.e., patient biting the endoscope. Once the patient has been adequately sedated with the intravenous medications, the endoscope is introduced into the upper esophagus and maneuvered down into the esophagus under direct visualization and into the gastric area. Once in the gastric area, the scope may be further advanced into the small bowel with manipulation. This allows the examiner to carefully examine the initial segment of the small bowel, the duodenal bulb, the gastric mucosa, and the esophagus. Biopsies may be obtained if necessary, and other therapeutic procedures can be performed. These therapeutic procedures include sclerotherapy, esophageal or pyloric dilation, electrocautery to control bleeding, or to remove foreign bodies. Once the diagnostic or therapeutic procedure has been completed, samplings or biopsies from the gastric area may be sent to the lab for further diagnostic studies. The mouthpiece is then removed from the patient and the patient is transferred to a recovery area. The recovery time is brief, usually about 10–15 minutes.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A mouthpiece to facilitate the introduction of a medical instrument into the esophagus of a patient, the mouthpiece comprising a hollow tubular structure with an outer convex flange to fit over the lip of the patient and an inner flange to fit inside the incisor teeth of the patient, an annular hollow-tubular connecting bridge member adapted to receive the biting action of said incisor teeth, said hollow being centrally located and extending from the outside of said outer flange to the inside of said inner flange, and an inwardly extending, downwardly curving elongated plate attached to the lower portion of said inner flange and adapted to lie above and to depress the patient's tongue.

2. The mouthpiece of claim 1 which is an integrally molded plastic article of manufacture.

3. The mouthpiece of claim 1 wherein said connecting bridge member is generally elliptical in lateral cross-section.

4. The mouthpiece of claim 3 wherein said hollow is elliptical with the long axis of the ellipse being generally horizontal when viewed from said outer flange.

5. The mouthpiece of claim 4 wherein said elliptical hollow at said outer flange has a long horizontal diameter of about 35–45 mm and a short vertical diameter of about 10–20 mm.

6. The mouthpiece of claim 1 wherein the longitudinal axis of said hollow is tilted upwardly from the horizontal from said outer flange to said inner flange.

7. The mouthpiece of claim 6 wherein the angle of tilt is about 15 degrees to 18 degrees.

8. The mouthpiece of claim 1 wherein said curving plate extends inwardly from the outer surface of said outer flange a horizontal distance of about 40–60 mm.

9. The mouthpiece of claim 1 wherein said hollow is generally elliptical with the long diameter of the ellipse being positioned horizontally.

10. A medical mouthpiece to be worn by a patient receiving an upper gastrointestinal endoscopy, said mouthpiece comprising a large elliptical lip cover plate spaced forwardly of a small tooth flange to fit inside the upper and lower incisors or the patient, a hollow tubular connecting member rigidly joining said lip cover plate to said tooth flange adapted to be clamped between said upper and lower incisors, said hollow extending from the outside of said lip cover plate to the inside of said tooth flange, and an inwardly extending, downwardly curving elongated tongue plate attached to the lower portion of said tooth flange and adapted to depress the patient's tongue and to guide an endoscope into the patient's esophagus.

\* \* \* \* \*